United States Patent
Paek et al.

(10) Patent No.: US 9,983,202 B1
(45) Date of Patent: May 29, 2018

(54) METHOD OF SYNTHESIZING POLYMERIC FLUORESCENT TRACER FOR SIGNAL AMPLIFICATION

(71) Applicant: Korea University Research and Business Foundation, Seoul (KR)

(72) Inventors: Se-Hwan Paek, Seoul (KR); Sung-Min Seo, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days. days.

(21) Appl. No.: 15/412,239

(22) Filed: Jan. 23, 2017

(51) Int. Cl.
*G01N 33/533* (2006.01)

(52) U.S. Cl.
CPC .................. *G01N 33/533* (2013.01)

(58) Field of Classification Search
CPC .................................................. G01N 33/533
See application file for complete search history.

(56) References Cited

U.S. PATENT DOCUMENTS

| | | | | |
|---|---|---|---|---|
| 2002/0146730 A1* | 10/2002 | Liu | ...................... | B01J 19/0046 435/6.19 |
| 2003/0059811 A1* | 3/2003 | Djaballah | ............ | G01N 33/542 435/6.11 |

OTHER PUBLICATIONS

Seo, Sung-Min et al., "A flourescent immunosensor for high-sensitivity cardiac troponin I using a spatially-controlled polymeric, nano-scale tracer to prevent quenching", Biosensors and Bioelectronics, 83 (2016) 19-26.

* cited by examiner

*Primary Examiner* — Samuel P Siefke
(74) *Attorney, Agent, or Firm* — Mintz Levin Cohn Ferris Glovsky and Popeo, P.C.; Kongsik Kim

(57) ABSTRACT

Disclosed is a method of synthesizing a polymeric fluorescent tracer for signal amplification, including (a) subjecting a streptavidin-fluorophore conjugate (SA-FL) and a spacer-attached biotin-conjugated antibody (b-Ab) to reaction at least two times; (b) treating a dual biotin oligomer spacer (db-oN); and (c) performing a homogenization process.

10 Claims, 6 Drawing Sheets

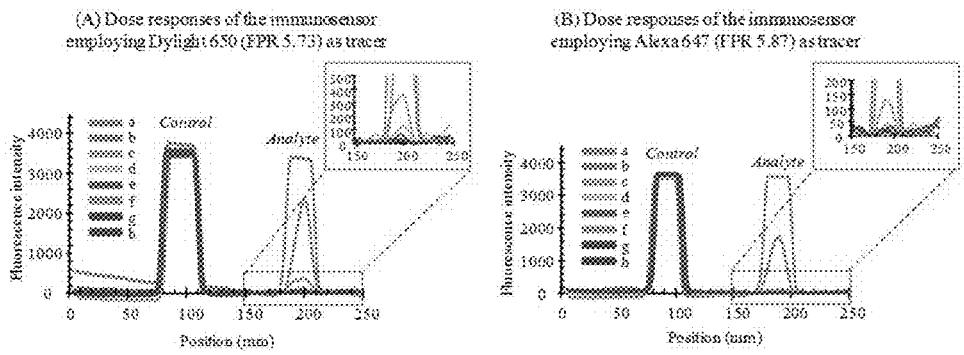
Standard curves for the rapid immunosensor system employing the
polymeric detection antibodies labeled with different fluorescent dyes
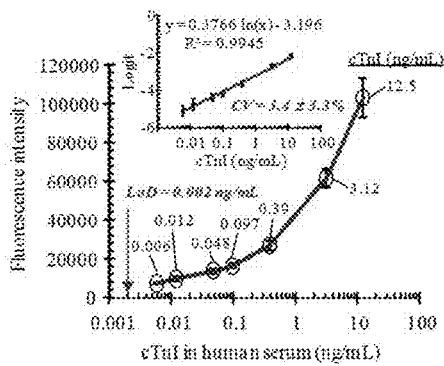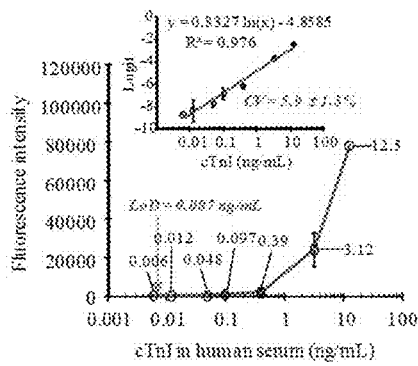
FIG. 5

Correlation test for the performances of the 2D-chromatographic immunosensor with those of commercial devices as reference systems
(A) Correlation in a whole concentration range (4-logs; 6 pg/mL ~ 12.5 ng/mL)
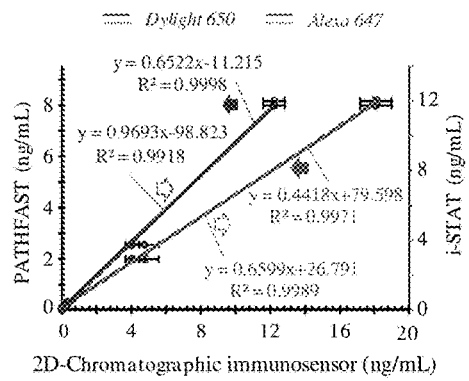
(B) Correlation in the sub-nano gram range (< 400 pg/mL)
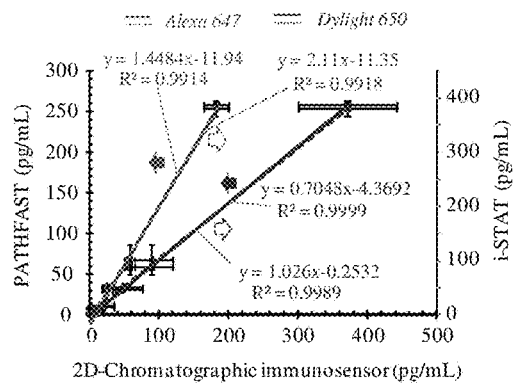
(C) Correlation at the low-dose range (< 100 pg/mL)
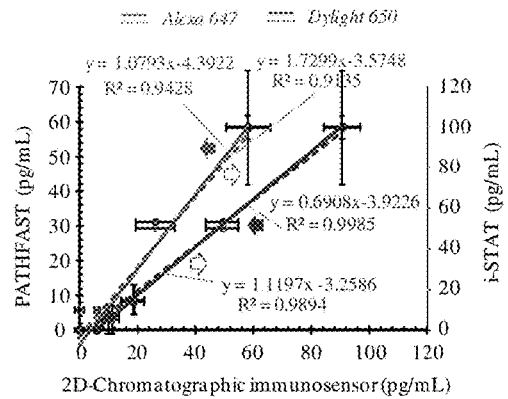
FIG. 6

METHOD OF SYNTHESIZING POLYMERIC FLUORESCENT TRACER FOR SIGNAL AMPLIFICATION

BACKGROUND OF THE INVENTION

1. Technical Field

The present invention relates to a bioassay material technique that may be applied to a signal amplification process in a variety of fields, including those of analytical chemistry, diagnostic testing, cell analysis, molecular imaging, etc.

2. Description of the Related Art

Signal amplification material technology for realizing high-sensitivity diagnosis in diagnostic testing fields has been proposed to attain competitiveness through the generation of high-sensitivity signals compared to signal tracers of existing diagnostic products and to ensure technical excellence in the market.

Many prior attempts have been made to amplify fluorescence signals. A fluorophore is a material in which internal electrons enter an excited state due to external excitation light energy, and this state is then sequentially turned into a ground state to thus emit photons. The extent of emission thereof is referred to as the quantum yield of the fluorophore. Here, when a fluorophore having a high quantum yield is used or a large amount of fluorophore is used, a further amplified signal may be obtained. However, when the distance between fluorophores is decreased to 10 nm or less, self-quenching occurs due to energy transfer, in which excited internal electron energy is transferred to a neighboring fluorophore without the emission of photons and the electrons thus enter a ground state, undesirably resulting in signal loss. Hence, conventional research using a fluorophore polymer probe is of limited use in diagnostic testing fields including those of immunoassays, etc., due to the self-quenching problem. Accordingly, signal loss can be caused due to self-quenching in fluorophore-coupled proteins or nucleotides synthesized via polymerization to contain a large amount of fluorescent material.

To overcome the quenching effect, a polymeric fluorescent tracer that decomposes to release dye at the time of signal generation has been developed. This was carried out by initially synthesizing dye molecules attached to a carrier such as protein or nucleotide, which is subsequently degraded enzymatically. Discharge of the dye into the liquid phase upon excitation produces the signal. However, use of such a fluorescent tracer in the solid phase, as in a lateral flow-type immunosensor, is problematic. Conversely, quenching can be utilized in signal generation by using two different fluorophores co-conjugated to a polymer backbone. In this format, the excited energy from one (donor) is transferred to the other (acceptor), which emits a signal at a higher wavelength than that of the first dye. This fluorescence resonance energy transfer (FRET) has been used for signal amplification, e.g., for AMI diagnosis. In devices for cardiac diagnosis, e.g., Triage Cardiac System, a fluorescent tracer, hybrid phthalocyanine, was produced by cross-linking phthalocyanine with naphthalocyanine, such that FRET occurred between the two dyes and so the signal was not decreased by self-quenching.

Moreover, there have been many reports on signal amplification in which a fluorophore is conjugated to streptavidin and the tracer is accumulated stepwise in a biotinylated detection antibody. Here, the kind of fluorophore that is mainly useful is limited only to quantum dots, which undergo less self-quenching through energy transfer even when the distance between the quantum dots is decreased. Furthermore, in a lateral flow-type point-of-care (POC) biosensor, such as a rapid diagnostic kit, washing and sequential signal generator supply are difficult, and thus limitations are imposed on the use of the aforementioned methods in POC fields. In addition, there are reports in which the fluorophore is conjugated to the biotin-poly-lysine backbone, and the resulting product is polymerized with a biotinylated detection antibody by means of streptavidin to give a polymer that is then employed as a signal amplifier in a lateral flow system. However, this method may cause self-quenching because the distance between the polymerized fluorophores in the polymer molecules is decreased due to the flexibility of poly-lysine. Also, poly-lysine is multiply connected to the biotinylated detection antibody, thus incurring steric hindrance during the reaction of the detection antibody.

SUMMARY OF THE INVENTION

Accordingly, the present invention has been made keeping in mind the above problems encountered in the related art, and the present invention is intended to provide a polymeric fluorescent tracer for signal amplification and a method of synthesizing the same, wherein any fluorophore may be used therefor, and the polymeric fluorescent tracer may be utilized as the signal generation source of a lateral flow-type rapid kit by enabling the formation of a three-dimensional nanoscale structure in advance.

The present invention provides a polymeric fluorescent tracer for signal amplification and a method of synthesizing the same, wherein any fluorophore may be used therefor and the polymeric fluorescent tracer may be utilized as a signal generation source of a lateral flow-type rapid kit by enabling the formation of a three-dimensional nanoscale structure in advance.

According to the present invention, the gradual preparation of a streptavidin-biotin reaction-based polymeric fluorescent tracer has been devised as a method able to supply a large amount of fluorophore while minimizing self-quenching. Specifically, even when a typical reaction principle for streptavidin-biotin reaction is employed, any commercially available fluorophore can be used in the present invention, in lieu of specific materials, such as a fluorophore having a high Stokes shift to minimize light interference between excitation and emission or quantum dots that undergo less self-quenching at close range. Therefore, the present invention provides a method of gradually synthesizing a polymeric fluorescent tracer so as to easily realize signal amplification using any commercially available fluorophore, by overcoming conventional problems in which a complicated chemical synthesis process or a specific fluorophore has to be used in order to obtain a high-sensitivity fluorescence signal. Since self-quenching occurs when fluorophore molecules approach to within a specific distance, a technique for manufacturing a three-dimensional nanoscale structure is provided such that multiple fluorophore molecules can be polymerized in a state of being spaced apart from each other by a predetermined interval. When the method of the invention is used, a high-sensitivity signal can be ensured using a typically useful fluorophore, without the use of a complicated chemical synthesis process or a specific fluorophore, such as quantum dots, thereby enabling early diagnosis and ultralow-concentration analysis in the diagnostic testing and analytical chemical fields, and also high-resolution analysis in the cell imaging examination fields.

BRIEF DESCRIPTION OF THE DRAWINGS

FIG. 5 shows the results of cardiac troponin I concentration response and a standard curve of an immunosensor using a DyLight 650 polymeric fluorescent tracer or an Alexa 647 polymeric fluorescent tracer as a signal generation source; and FIG. 6 shows the correlation results between the performance of an immunosensor using the polymeric fluorescent tracer of the invention and the performance of existing sensor systems.

DESCRIPTION OF THE SPECIFIC EMBODIMENTS

Figure 1:
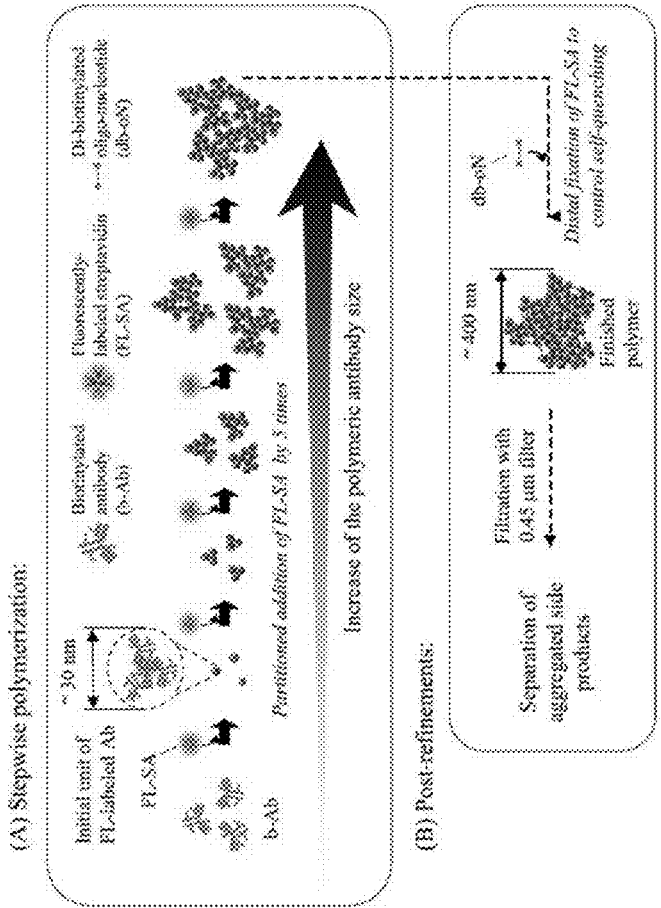
FIG. 1 shows the stepwise synthesis of a polymeric fluorescent tracer and post-refinement.

The present invention pertains to a method of synthesizing a polymeric fluorescent tracer for signal amplification and a polymeric fluorescent tracer for signal amplification synthesized using the method, wherein any fluorophore may be utilized by virtue of a gradual polymerization process, and a three-dimensional nanoscale structure may be provided in advance, and thus such a polymeric fluorescent tracer may be used as a signal generation source of a lateral flow-type rapid kit.

Specifically, the present invention addresses a method of synthesizing a polymeric fluorescent tracer for signal amplification, comprising the steps of: (a) subjecting a streptavidin-fluorophore conjugate (SA-FL) and a spacer-attached biotin-conjugated antibody (b-Ab) to reaction at least two times; (b) treating a dual biotin oligomer spacer (db-oN); and (c) performing a homogenization process.

Below is a detailed description of respective steps of the method of synthesizing the polymeric fluorescent tracer for signal amplification according to the present invention.

Step (a)

In this step, the streptavidin-fluorophore conjugate (SA-FL) and the spacer-attached biotin-conjugated antibody (b-Ab) are reacted at least two times.

The streptavidin-fluorophore conjugate (SA-FL) and the spacer-attached biotin-conjugated antibody (b-Ab) are preferably reacted at a final molar ratio ranging from 0.5:1 to 2:1, and more preferably 1.25:1. The streptavidin-fluorophore conjugate (SA-FL) is stepwise added until the above final molar ratio is achieved. For example, in the case where the final molar ratio of the streptavidin-fluorophore conjugate (SA-FL) and the spacer-attached biotin-conjugated antibody (b-Ab) is 1.25:1 through three reactions, 0.4167 mol of the streptavidin-fluorophore conjugate (SA-FL) is added three times so that SA-FL is finally supplied in an amount of 1.25 mol. Also, in the case where the final molar ratio of the streptavidin-fluorophore conjugate (SA-FL) and the spacer-attached biotin-conjugated antibody (b-Ab) is 1.25:1 through five reactions, 0.25 mol of the streptavidin-fluorophore conjugate (SA-FL) is added five times, so that SA-FL is finally added in an amount of 1.25 mol. When the polymerization is carried out at the above ratio through stepwise addition in this way, the aggregation of the residual functional group depending on the concentration gradient and the molar ratio may be prevented, because the reaction of the streptavidin-fluorophore conjugate (SA-FL) and the spacer-attached biotin-conjugated antibody (b-Ab) is a biding reaction that depends on the concentration and the molar ratio.

The kind of fluorophore that is useful in the present invention is not particularly limited, but examples thereof may include acridine dyes, cyanine dyes, fluorine dyes, oxazine dyes, phenanthridine dyes, and rhodamine dyes, such as Calcein, Coumarin, Cy3, Cy5, SYBR Green, DAPI, Luciferin, TAMRA, FAM, ROX, HEX, Texas Red, DyLight and Alexa.

The spacer attached to biotin functions to bind biotin of the antibody (b-Ab) and the streptavidin-fluorophore conjugate (SA-FL) while keeping them spaced apart from each other by a predetermined distance upon the reaction of biotin and streptavidin. When a plurality of streptavidin-fluorophore conjugates (SA-FL) is attached to a single antibody, two or three groups of streptavidin-fluorophore conjugates (SA-FL) are bound at a predetermined interval by means of the spacer having a predetermined length, whereby self-quenching of the fluorophores at close range may be physically prevented. Preferably, the spacer-attached biotin is LC-biotin to which a 4 to 8 Å long spacer (LC: Long Chain) is attached, or LC-LC-biotin to which two spacers each having a length of 4 to 8 Å are attached.

This antibody is preferably at least one selected from among a monoclonal antibody, a polyclonal antibody, and a fragmented antibody. In addition to the antibody, DNA, RNA, PNA or a lipid bilayer, to which the spacer-attached biotin may be conjugated, may be utilized.

The reaction in step (a) is preferably carried out five to ten times, and this gradual reaction is responsible for preventing aggregation depending on the concentration gradient during the reaction between the streptavidin-fluorophore conjugate (SA-FL) and the spacer-attached biotin-conjugated antibody (b-Ab), and enables the uniform distribution thereof.

Step (b)

This step includes treating the dual biotin oligomer spacer (db-oN).

The dual biotin oligomer spacer (db-oN) is configured such that biotin is conjugated to both ends of the oligomer spacer. After the completion of the reaction between the streptavidin-fluorophore conjugate (SA-FL) and the spacer-attached biotin-conjugated antibody (b-Ab), the residual streptavidin functional group of the streptavidin-fluorophore conjugate (SA-FL) is blocked by the biotin of the oligomer spacer, and also, the streptavidin-fluorophore conjugates (SA-FL) are interconnected in three dimensions and distally fixed to each other while being maintained as long as the length of the oligomer spacer due to the biotin conjugated to both ends of the oligomer spacer. Taking into consideration the streptavidin having an average size of 5 nm and a single oligomer having an average size of 0.34 nm (3.4 Å), the length of the oligomer spacer is preferably set to the range of about 12 mer (average length of 4.08 nm) to 22 mer (average length of 7.48 nm), but the present invention is not limited thereto. The long oligomer spacer is bent, making it difficult to form a rigid three-dimensional structure configured such that the streptavidin-fluorophore conjugate (SA-FL) and the spacer-attached biotin-conjugated antibody (b-Ab) are bound to each other. On the other hand, the short oligomer spacer is insufficient to interconnect streptavidin molecules having an average size of 5 nm in the streptavidin-fluorophore conjugates (SA-FL). Hence, the length of the oligomer spacer is regarded as important. This step is unrelated to the base sequence of the oligomer spacer, but base sequences of the oligomer spacer that result in the formation of a hairpin or loop through internal hybridization are preferably excluded. Typically, 12 to 22 base sequences are favorably synthesized, and feasible poly A and poly T are mainly used as the base sequences of the oligomer spacer.

In step (b), the dual biotin oligomer spacer (db-oN) is supplied, whereby the residual streptavidin active sites of SA-FL conjugates are blocked, and also, the SA-FL conjugates are distally fixed to each other while being maintained as long as the length of the oligomer spacer due to the biotin at both ends of db-oN, thereby forming a three-dimensional nanoscale structure.

Step (c)

This step includes performing a homogenization process.

Specifically, filtration with a micrometer filter is carried out.

Through this step, a polymeric fluorescent tracer having a predetermined size may be formed. In the present invention, the polymeric fluorescent tracer preferably has a size of 300 nm to 400 nm. The streptavidin-fluorophore conjugate (SA-FL) having an average size of 5 to 6 nm and the spacer-attached biotin-conjugated antibody (b-Ab) having an average size of 14 nm are reacted and bound at a molar ratio of 0.5:1 to 2:1, and preferably 1.25:1, and are then distally fixed in the form of a three-dimensional nanoscale structure using an oligomer spacer (db-oN) having an average length of 4.08 to 7.48 nm. Thereby, a three-dimensional nanoscale structure having an average size of 300 to 400 nm is mainly formed taking into consideration the average size of each material.

In addition, the present invention addresses a polymeric fluorescent tracer for signal amplification, synthesized by the above method.

In addition, the present invention addresses a sensor including the polymeric fluorescent tracer for signal amplification. The sensor of the present invention exhibits remarkably improved sensitivity and analysis performance.

A better understanding of the present invention may be obtained via the following examples, which are merely set forth to illustrate but are not to be construed to limit the scope of the present invention, and such examples may be appropriately modified and altered by those skilled in the art within the scope of the invention.

Example 1: Preparation of Polymeric Fluorescent Tracer Through Gradual Synthesis at Least Two Times and Size Homogenization (1) Gradual Synthesis at Least Two Times (Desirably, Five Times)

A gradual synthesis process was developed in a manner in which a polymeric fluorescent tracer was prepared while spacing fluorophore molecules apart from each other by a predetermined distance so as to prevent self-quenching during the synthesis process (FIG. 1). For gradual synthesis, conjugation of a fluorophore to streptavidin was carried out at an optimal fluorophore/protein molar ratio (FPR) in consideration of the quantum yield per fluorophore. This is intended to minimize self-quenching when the streptavidin molecule is labeled with the fluorophore (e.g. Alexa 647). When streptavidin-fluorophore (SA-FL) conjugates are provided in the form of a bundle at a predetermined distance between the SA-FL conjugates, self-quenching is minimized and a large number of fluorophores may be supplied. In order to achieve gradual attachment while maintaining a predetermined interval, the SA-FL conjugate and the 3 nm long spacer-attached biotin-conjugated antibody (b-Ab) at a molar ratio of 0.25:1 were stepwise added five times, so that the final molar ratio thereof was 1.25:1 (FIG. 1, (A)). After addition five times, db-oN, in which biotin was conjugated to both ends of the 17-mer oligomer, was supplied, whereby the residual streptavidin active sites of SA-FL were blocked, and simultaneously SA-FL conjugates were interconnected due to biotin at both ends of db-oN, ultimately forming a three-dimensional nanoscale structure (FIG. 1, (B)).

(2) Size Homogenization

In order to homogenize the size of the gradually synthesized polymeric fluorescent tracer, it was filtered with a 0.45 micrometer filter, whereby a polymeric fluorescent tracer having a predetermined size (395±56 nm) was formed (FIG. 2, Five-step reaction), in which multiple fluorophores were spaced apart from each other at a predetermined interval.

Figure 2:
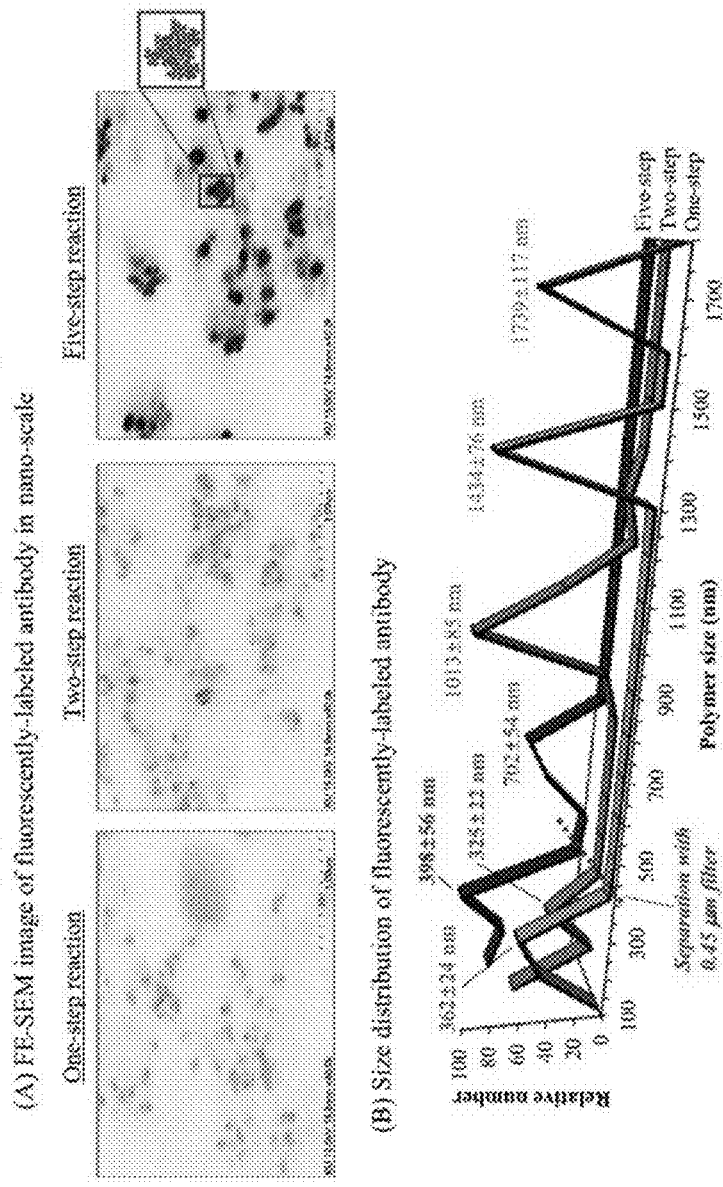
FIG. 2 shows the characterization of a three-dimensional nanoscale polymer, formed through stepwise polymerization.

Test Example 1: Comparison with Polymeric Fluorescent Tracer Obtained without Gradual Synthesis Reaction Gradual polymerization through five-step reaction, as in Example 1, was not performed, the same amount of SA-FL was added all at once to b-Ab, and polymerization was performed, in which case it was difficult to manufacture a polymeric fluorescent tracer in which multiple fluorophores were spaced apart from each other at a predetermined interval (FIG. 2, One-step reaction).

Figure 3:
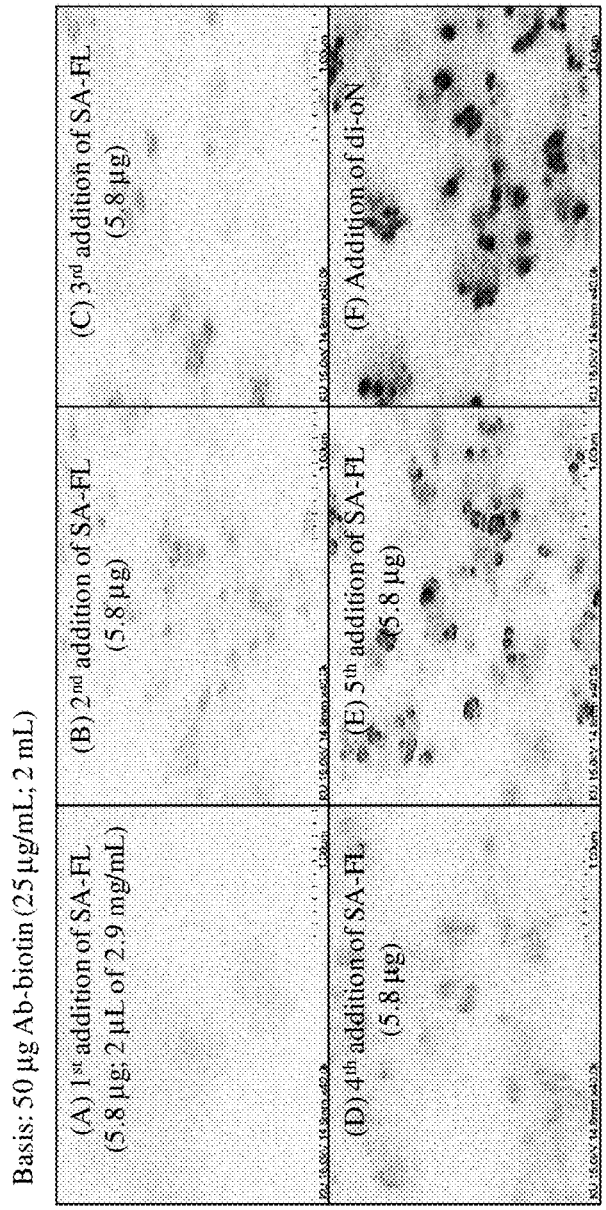
FIG. 3 shows FE-SEM imaging monitoring results for five-step gradual polymerization and post-refinement.

The stepwise synthesis of SA-FL and b-Ab at a predetermined molar ratio supplied five times and the introduction of the oligomer spacer (db-oN) for maintaining a predetermined distance are intended to polymerize multiple fluorophore molecules while being spaced apart from each other at a predetermined distance (FIG. 3).

Accordingly, a polymeric fluorescent tracer comprising multiple fluorophores spaced apart from each other at a predetermined interval can be formed using a widely used fluorophore in the aforementioned manner, without the use of a conventional complicated chemical synthesis process or quantum dots (e.g. fluorophore synthesized to induce FRET). When such a polymeric fluorescent tracer is used as a signal generation source upon immunoassay, self-quenching due to a large number of fluorophores can be minimized, thus obtaining a signal amplification effect.

Figure 4:
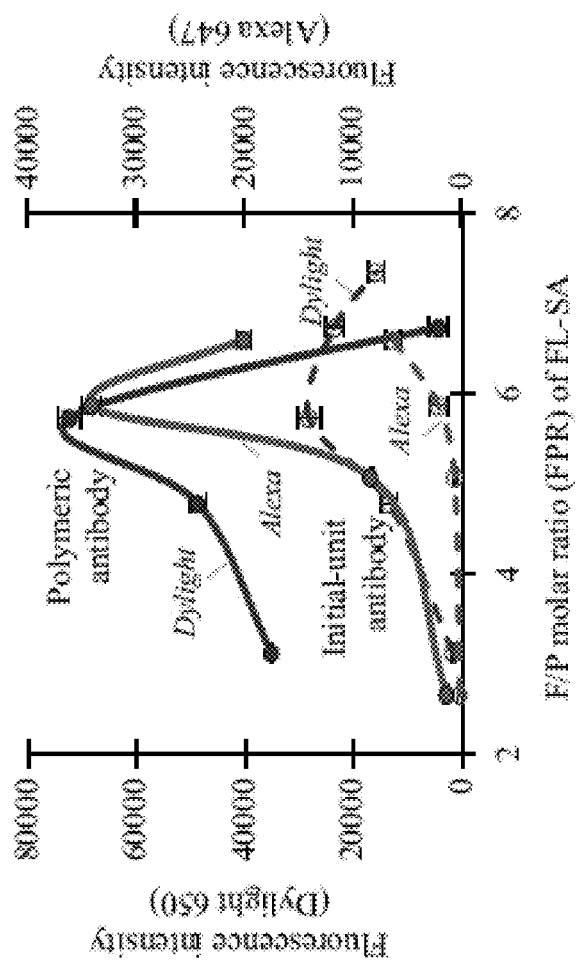
FIG. 4 shows the optimal fluorophore/protein molar ratio (FPR) depending on the kind of fluorophore (DyLight 650, Alexa 647) upon the preparation of a streptavidin-fluorophore conjugate (SA-FL)

Test Example 2: Evaluation of Signal Amplification Effect of Polymeric Fluorescent Tracer of the Invention In order to evaluate the actual signal amplification effect of the polymeric fluorescent tracer, gradual synthesis was performed using a DyLight 650 fluorophore and an Alexa 647 fluorophore. During the formation of the SA-FL conjugate, which was achieved by attaching each fluorophore to streptavidin, the fluorophore-to-streptavidin ratio, that is, the fluorophore/protein molar ratio (FPR), was 5.73 when using the DyLight 650 and was 5.87 when using the Alexa 647 because the signal was the highest at the corresponding ratio (FIG. 4). The SA-FL thus manufactured was used. The DyLight 650 SA-FL and the Alexa 647 SA-FL were separately added to b-Ab at a molar ratio of 0.25:1, whereby five-step gradual synthesis was carried out. As shown in FIG. 1, a polymeric fluorescent tracer was prepared using SA-FL as a core.

The DyLight 650 and Alexa 647 polymeric fluorescent tracers were respectively applied to a rapid immunosensor, and the response of the sensor and the detection sensitivity were measured depending on the concentration of cardiac troponin I in the serum (FIG. 5). In the case of the DyLight 650 polymeric fluorescent tracer, the detection sensitivity was 0.002 ng/mL, an average CV in the 4-log concentration range was 3.4±3.3%, and the linearity of the concentration response curve was $R^2>99\%$ (FIG. 5, (A)). In the case of the Alexa 647 polymeric fluorescent tracer, the detection sensitivity was 0.007 ng/mL, the CV in the 4-log concentration range was 5.9±1.5%, and the linearity of the concentration response curve was $R^2>97\%$ (FIG. 5, (B)). When comparing these results with sensitivity, measured by means of the same sensor using a conventional simple fluorescence signal generation source, instead of the polymeric fluorescent tracer, the sensor using the DyLight 650 polymeric fluorescent tracer exhibited analysis performance that was increased by about 50 times and the sensor using the Alexa 647 polymeric fluorescent tracer exhibited analysis performance that was increased by about 14 times.

The performance of the sensor using, as the signal generation source, the DyLight 650 polymeric fluorescent tracer or the Alexa 647 polymeric fluorescent tracer was compared with the performance of commercially available sensor products. Examples of the commercially available sensor products are the PATHFAST, a small automatic immunoassay device made by Mitsubishi, and the i-STAT, a POC rapid diagnostic sensor made by Abbott. For the correlation comparison, cardiac troponin I was added to the serum to make a standard sample, and the analysis performance of each sensor for the sample was measured at the same time and the measurement correlations thereof were compared (FIG. 6).

The cardiac troponin I standard sample in the normal group serum concentration of 0.006 to 12.5 ng/mL was evaluated using the sensor including the DyLight 650 polymeric fluorescent tracer, and the results thereof were compared with those of PATHFAST and i-STAT products, whereby the correlation of 99% or more was shown in each of a whole concentration range (4-log) and a concentration range of <0.4 ng/mL (FIG. 6, (A) and (B)). The sensor including the DyLight 650 polymeric fluorescent tracer manifested a correlation of 94% or more with the PATHFAST product in a low concentration range of <0.1 ng/mL and a correlation of 91% or more with the i-STAT product (FIG. 6, (C)).

In the sensor using the Alexa 647 polymeric fluorescent tracer, the sample was measured in the diluted cardiac troponin I concentration range of 0.006 to 12.5 ng/mL in the normal group serum, as in the DyLight 650 fluorophore. Based on a comparison of the results with those of the PATHFAST and i-STAT products, a correlation of 99% or more was exhibited in each of a whole concentration range (4-log) and a concentration range of <0.4 ng/mL (FIG. 6, (A) and (B)). It exhibited a correlation of 99% or more with the PATHFAST product in a low concentration range of <0.1 ng/mL and a correlation of 98% or more with the i-STAT product (FIG. 6, (C)).

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of synthesizing a polymeric fluorescent tracer for signal amplification, comprising steps of:
   (a) subjecting a streptavidin-fluorophore conjugate (SA-FL) and a spacer-attached biotin-conjugated antibody (b-Ab) to reaction at least two times;
   (b) treating a dual biotin oligomer spacer (db-oN); and
   (c) performing a homogenization process,
   wherein the step (b) comprises supplying the dual biotin oligomer spacer (db-oN) so that a residual streptavidin active site of SA-FL is blocked and SA-FL conjugates are interconnected due to biotin at both ends of db-oN, thereby forming a three-dimensional nanoscale structure.

2. The method of claim 1, wherein in the step (a), a molar ratio of the streptavidin-fluorophore conjugate (SA-FL) and the spacer-attached biotin-conjugated antibody (b-Ab), subjected to reaction at least two times, is 0.5:1 to 2:1.

3. The method of claim 1, wherein in the step (a), the fluorophore is an acridine dye, a cyanine dye, a fluorine dye, an oxazine dye, a phenanthridine dye, or a rhodamine dye, including Calcein, Coumarin, Cy3, Cy5, SYBR Green, DAPI, Luciferin, TAMRA, FAM, ROX, HEX, Texas Red, DyLight or Alexa.

4. The method of claim 1, wherein in the step (a), the spacer-attached biotin is LC-biotin to which a spacer (LC: Long Chain) having a length of 4 to 8 Å is attached, or LC-LC-biotin to which two spacers each having a length of 4 to 8 Å are attached.

5. The method of claim 1, wherein in the step (a), the antibody is at least one selected from among a monoclonal antibody, a polyclonal antibody, and a fragmented antibody.

6. The method of claim 1, wherein in the step (a), the reaction is carried out five to ten times.

7. The method of claim 1, wherein in the step (b), the oligomer spacer (db-oN) has a length of 12 mer to 22 mer.

8. The method of claim 1, wherein the step (c) comprises performing filtration with a micrometer filter.

9. A polymeric fluorescent tracer for signal amplification, synthesized by the method of claim 1.

10. A sensor, comprising the polymeric fluorescent tracer of claim 9.

* * * * *